United States Patent [19]

Stewart

[11] Patent Number: 5,066,291
[45] Date of Patent: Nov. 19, 1991

[54] SOLID-STATE LASER FREQUENCY CONVERSION SYSTEM

[75] Inventor: Bob W. Stewart, Cincinnati, Ohio

[73] Assignee: Cincinnati Sub-Zero Products, Inc., Cincinnati, Ohio

[21] Appl. No.: 514,198

[22] Filed: Apr. 25, 1990

[51] Int. Cl.$^5$ .................... A61B 17/00; H03F 7/00
[52] U.S. Cl. ............................. 606/3; 128/395; 606/11; 359/326
[58] Field of Search ............. 372/23, 22, 25; 128/395; 606/3, 10, 11

[56] References Cited

U.S. PATENT DOCUMENTS

| | | | |
|---|---|---|---|
| 3,382,343 | 5/1968 | Muncheryan | 372/25 |
| 3,750,670 | 8/1973 | Palanos et al. | 606/3 |
| 3,988,593 | 10/1976 | Dewey, Jr. et al. | 307/88.3 |
| 4,180,751 | 12/1979 | Ammann | 307/428 |
| 4,189,652 | 2/1980 | Levinos et al. | 307/428 |
| 4,213,060 | 7/1980 | Byer et al. | 307/426 |
| 4,336,809 | 6/1982 | Clark | 606/3 |
| 4,456,657 | 6/1984 | Byer | 372/18 |
| 4,503,854 | 3/1985 | Jako | 606/11 |
| 4,520,816 | 6/1985 | Schachar et al. | 606/11 |
| 4,639,923 | 1/1987 | Tang et al. | 372/21 |
| 4,672,969 | 6/1987 | Dew | 606/3 |
| 4,739,507 | 4/1988 | Byer et al. | 372/22 |
| 4,791,927 | 12/1988 | Menger | 606/10 |
| 4,809,291 | 2/1989 | Byer et al. | 372/75 |
| 4,836,203 | 6/1989 | Müller | 606/3 |
| 4,880,996 | 11/1989 | Peterson et al. | 307/425 |
| 4,956,843 | 9/1990 | Akhavan-Leilabady et al. | 372/23 |

FOREIGN PATENT DOCUMENTS

| | | | |
|---|---|---|---|
| 1195737 | 10/1985 | Canada | 372/23 |
| 2809007 | 9/1979 | Fed. Rep. of Germany | 128/395 |
| 2633105 | 12/1989 | France | 128/395 |
| 8501445 | 4/1985 | World Int. Prop. O. | 128/395 |

OTHER PUBLICATIONS

Michael D. Jones et al. "Milliwatt-Level 213 nm Source Based on a Repetitively Q-Switched CW--Pumped Nd:YAG Laser", *IEEE Journal of Quantum Electronics*, vol. QE-15, No. 4, Apr. 1979, pp. 204-206.

"Analyses of Frequency Conversion and Application of New Non-Linear Crystals", J. T. Lin, p. 262.

"Generation of 1.54 Micron Radiation from YAG--Pumped Raman Media and Non-Linear Crystals", J. T. Lin, p. 187.

"Laser Surgery: $Co_2$ or HF", Myron L. Wolbarsht, 1984.

"An Extension of the Three-Zone Model to Predict Depth of Tissue Damage Beneath Er:YAG and Ho- (List continued on next page.)

Primary Examiner—James E. Davie
Attorney, Agent, or Firm—Frost & Jacobs

[57] ABSTRACT

There is provided a conversion system for use with commercially available laser devices for medical applications where laser light at a predetermined wavelength is converted for simultaneous coaxial application of laser light at a plurality of predetermined medically useable wavelengths. The conversion system includes focusing structure for focusing laser radiation at predetermined pump wavelength into a conversion medium. The conversion medium is prepared for efficient conversion of a portion of the radiation at the input pump wavelength to a signal wavelength, wherein, in one preferred application, either the pump or signal wavelength is in a range of between about 2.7 and about 3.25 microns. The system further includes structure for coaxially transmitting laser radiation at the resulting plurality of wavelengths from the conversion system for simultaneous use. In other preferred embodiments, the wavelength of the difference frequency produced by the conversion medium is also in a medically desirable range which can add to the effectiveness of the coaxial pump and signal wavelengths in particular medical applications. The conversion system thereby enables relatively unlimited adaption of commercially available laser devices to optimize the effectiveness and application of such devices for a variety of medical procedures.

32 Claims, 4 Drawing Sheets

OTHER PUBLICATIONS

:YAG Laser Excisions", Alan L. McKenzie, Phy. Med. Biol., 1989, vol. 34, No. 1,.

"Formation and Applications of Ring Profile Laser Beams", He Hailin, Oct. 1986.

"Combination Studies on Hyperthermia Induced by the Neodymium Yttrium Aluminum Garnet (Nd:YAG) Laser as an Adjuvant to Photodynamic Therapy", Thomas S. Mang, *SPIE*, vol. 847, pp. 158–162.

"Photodynamic Therapy Alone or in Conjunction with Near-Infrared Light-Induced Hyperthermia in Human Malignant Tumors. A Methodological Case Study", S. Andersson-Engels, *SPIE*.

"French Develop 'Four-In-One' PDT Laser", *Laser Focus World*, Mar. 1990, pp. 95–96.

"Bronchoscopic Phototherapy for Malignancies of the Tracheobronchial Tree", Eric S. Edell et al., *Laser in Medicine and Surgery*, pp. 137–141 (1987).

"Medical Applications of Lasers", Thomas F. Deutsch, *Physics Today*, Oct. 1988, pp. 56–63.

"Computer Controlled Contact Nd:YAG Laser System for Interstitial Local Hyperthermia and PTD", Norio Daikuzono et al., *SPIE*, vol. 907, pp. 75–79, *Laser Surgery: Characterization and Therapeutics* (1988).

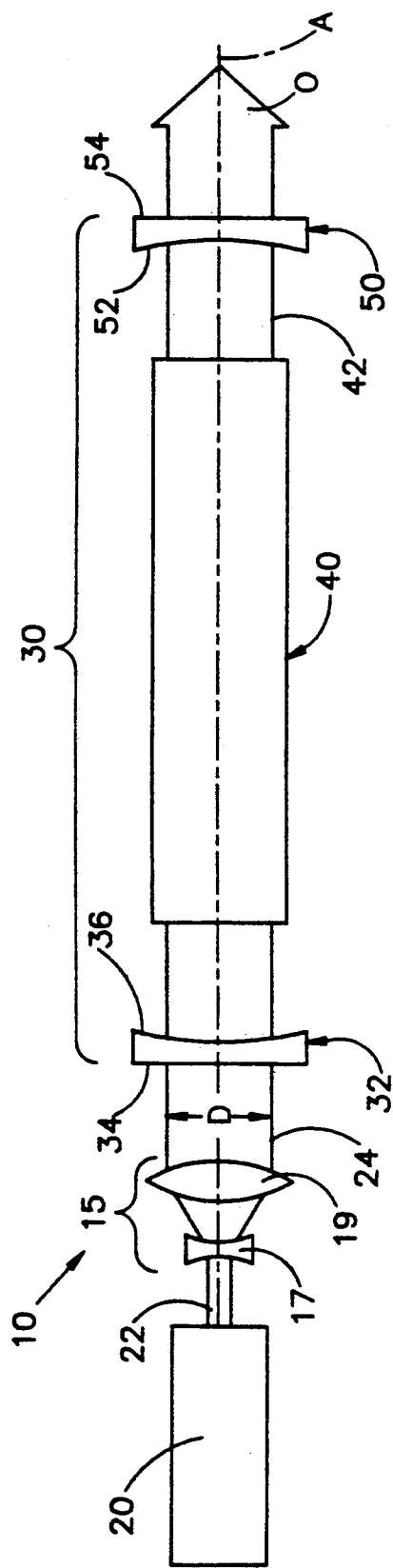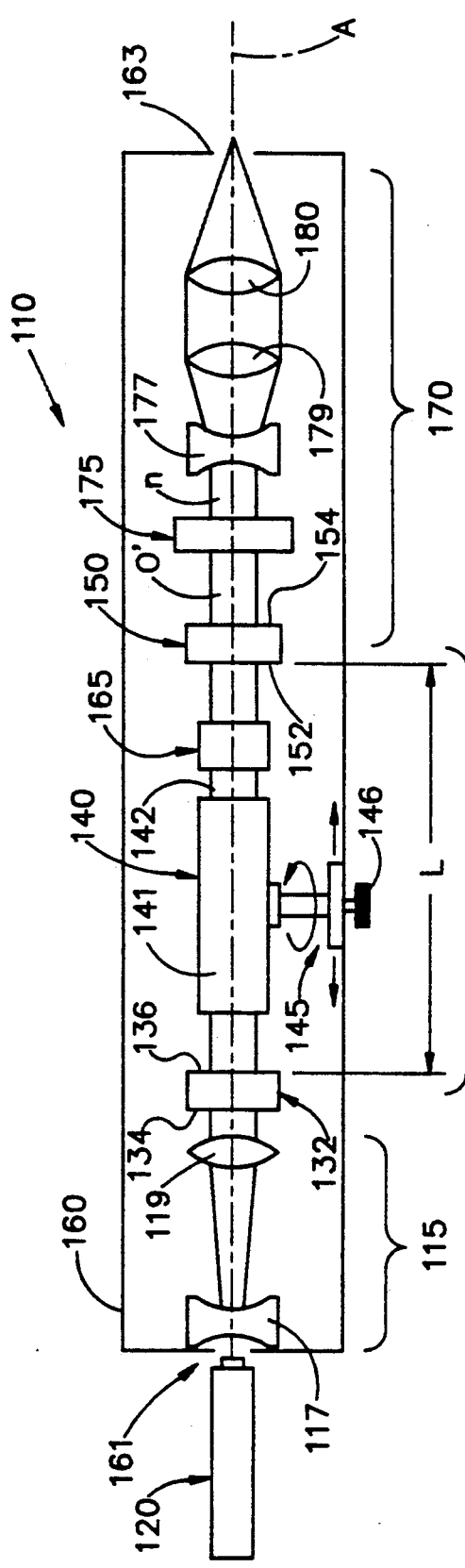

SOLID-STATE LASER FREQUENCY CONVERSION SYSTEM

TECHNICAL FIELD

This invention relates to an apparatus and method for converting the wavelength of coherent light into two predetermined wavelengths for coaxial transmission and simultaneous use, and, more particularly, to a solid-state laser conversion system and method for converting a pump wavelength of a laser light beam into a single output laser light beam having a predetermined mixture of pump and signal wavelengths for simultaneous use.

BACKGROUND ART

The development and use of laser systems in surgery and other medical applications continues to expand at an ever increasing rate as new technology becomes available and new applications for lasers are discovered. Currently used surgical laser systems include the $CO_2$ laser device which produces a light beam having a wavelength of 10.6 microns, and solid-state devices such as the Nd:YAG laser (Neodymium Yttrium Aluminum Garnet, $Y_3Al_5O_{12}$) laser, which produces a light beam having a wavelength of approximately 1.064 microns, the argon-ion laser producing a light beam having a wavelength of approximately 0.5145 microns (or 514.5 nm), the Erbium:YAG (Er:YAG) laser producing a light beam having a wavelength of approximately 2.9 microns, the Holmium:YAG (Ho:YAG) laser producing a light beam having a wavelength of approximately 2.1 microns, and, more recently, a frequency-doubled Nd YAG laser producing a light beam having a wavelength of approximately 0.532 microns (532 nm). Heretofore, however, the Er:YAG and Ho:YAG lasers have been being used only in experimental applications, as they have yet to obtain universal approval for clinical use.

It has been found that because human tissue is approximately 80% water, the absorption of radiation energy (i.e. light energy) in water will determine the characteristics of laser interaction in tissue. The $CO_2$ laser has been found to provide a very good "light knife" due to its ability to induce incisions with less charring with good hemostatic control; however, the Nd:YAG laser has better photocoagulative ability, as its 1.064 micron wavelength penetrates much deeper into tissue than the 10.6 micron radiation, and is closer to the hemoglobin absorption peak (i.e. approximately 0.577 microns). Because the water absorption peak has been found to be approximately 2.9 microns, the Er:YAG laser is of special interest as providing an optimum "light knife" whose light beam wavelength is much closer to the absorption peak of hemoglobin (i.e. blood), and should theoretically provide better coagulative effects in conjunction with its superb cutting abilities. In practice, however, it has been observed that Er:YAG radiation is absorbed so strongly by the water content of the tissue that it provides very poor hemostasis.

On the other hand, it has been established by theory and experiment that a relationship exists between the time which tissue is exposed to light beam energy and the size of the surrounding zone of thermal damage caused by that light beam. It has been found that rapid, short "bursts" or "pulses" of laser light can help to minimize the surrounding zone of thermal damage caused by laser cutting. Because the Er:YAG laser technology is relatively new and immature, and because of the relatively longer wavelength of its output, efficient technology capable of providing short pulses of the output radiation is not available. In contrast, the relatively well developed technology of the Nd:YAG laser can provide electro-optical pulsing (Q-switched technology) which can be up to 100 times shorter than the relatively crude pulsing technology currently available for Er:YAG lasers. Similarly, reliable pulsing technology has yet to be developed for Ho:YAG lasers.

Consequently, while the Er:YAG and Ho:YAG lasers provide laser radiation at wavelengths much closer to the absorption peak of water, the inability to precisely control the temporal application of such radiation tends to result in increased thermal diffusion beneath the laser excision, which can result in increased inflammatory response within the tissue, delaying healing and increasing the chances of post operative infection. Another laser delivery system known as the HF laser can also produce laser radiation at a wavelength of approximately 2.9 microns, however, the use of the HF laser in medical applications is felt by many to be inappropriate because of the large size of the device and the use flowing $SF_6$—a toxic gas—to produce free fluorine).

The 1.064 micron wavelength output of the Nd:YAG laser provides better coagulative features as a result of relatively deeper penetration into the tissue and resultant enhanced hemostatic control. On the other hand, a light beam at the 1.064 micron wavelength creates inferior incisions as increased charring of surrounding tissue is created. In fact, as the wavelength of a particular laser light beam is decreased toward the Hemoglobin absorption peak (i.e. between approximately 0.5 and 0.6 microns), the ability for hemostatic control increases, while the precision or "cleanness" of the incision decreases. While a particular laser can sometimes be chosen for optimum surgical conditions (such as in cornea surgery where there is no bleeding and optimal incision control can be obtained by utilizing a laser which produces radiation at a wavelength within the peak of the water absorption spectrum of 2.85 to 2.95 microns), too often a tradeoff must be made between the surgeon's desire to obtain the most precise and clean incision, and a desire to minimize thermal damage and to optimize hemostasis. Additionally, due to the relatively high cost of laser equipment, rarely does a physician have the luxury of choosing between several types of laser devices for any particular surgical procedure.

Because a variety of solid-state laser devices are available in the industry which provide laser radiation at wavelengths in the relatively longer ranges of the spectrum (i.e. 0.700–3.0 microns), it has not been uncommon to utilize available technology for doubling the frequency of the output of one of these devices to reduce the wavelength to the visible spectrum and/or to provide laser energy closer to the absorption peak of hemoglobin for increased hemostatic control. U.S. Pat. Nos. 4,639,923, 4,739,507, and 4,809,291 are examples of devices which provide for doubling of frequencies to reduce the wavelength of laser radiation provided by a particular laser device. While frequency doubling can reduce the resultant power provided by any particular laser device by 30% or more, this procedure often represents the only practical way of obtaining laser radiation to provide for visible laser light and/or increased hemostatic control.

For example, laser radiation from the Nd:YAG laser can be frequency doubled by utilization of well-known and relatively readily available KTP (KTiOPO₄) crystals or Beta-Barium-Borate (B—BaB₂O₄ or BBO) crystals to provide laser radiation at a wavelength of 0.532 microns. While laser radiation at a wavelength of approximately 0.577 microns can be provided with a dye laser system, this wavelength cannot be produced by currently available solid-state systems, which are much preferred for surgical application due to their reliability and ease of use and maintenance.

Optical parametric oscillator (OPO) technology has also been utilized to convert laser radiation to longer wavelengths in a more reliable solid-state form. U.S. Pat. No. 4,180,751 includes a description of the utilization of an OPO device to provide a signal or idler frequency from a pump wavelength. OPO is the inverse of sum-frequency generation processes like second harmonic generation. In OPO conversion, two variable frequencies, related as follows:

$$\frac{1}{\lambda p} = \frac{1}{\lambda 1} + \frac{1}{\lambda 2},$$

where λp is the pump wavelength, are determined by the particular phase matching used. Only one pair of frequencies can be phase matched at a time. By adjusting the phase matching parameters, e.g., the temperature or orientation of the non-linear crystal in an OPO setup, the output can be "tuned" over a range of frequencies. In OPO arrangements, the pump wavelength is always converted into two longer wavelength components, λ1 and λ2.

Other efforts have been directed to providing laser light at a single optimal wavelength which could provide satisfactory cutting and coagulative abilities. In fact, the development of the Ho:YAG laser with its 2.1 micron output is understood to have been the result of just such a study. No such optimal single wavelength has been identified, however, as results generally show inferior cutting and inferior sealing.

It has been speculated that a compound laser system capable of producing the cleanness of incision of a CO₂ laser or an Er:YAG laser, along with the photocoagulative ability and hemostatic control of, for example, a frequency doubled Nd:YAG laser would be a valuable surgical tool. As set forth in his article titled "Laser Surgery: CO₂ or HF", Myron L. Wolbarsht (IEEE J. Quantum Electronics, QE-20, No. 12, December, 1984), such a compound laser system was envisioned as literally incorporating several laser types available for simultaneous use. Wolbarsht specifically suggested the use of HF laser technology for optimum cutting, and an argon-ion or Nd:YAG laser for deeper penetration and increased coagulation. As set forth above, the size and toxic nature of the gas of the HF device makes it a poor match for use in surgical applications, and the combination of two expensive laser devices would not only be cost prohibitive, but would also be difficult to structurally arrange for convenient and accurate use. Moreover, the development of fiber optic delivery systems for the CO₂ wavelength laser continues to lag far behind those for other medically useful wavelengths such as the 1.064 micron YAG laser. In any event, no such device has been made available in the industry.

Consequently, heretofore there has not been provided a single practical device for delivering a single laser light beam having two or more medically useable wavelengths which could, for example, optimize simultaneous cutting and sealing in a single operation. Moreover, there has not been available a solid-state laser which can simultaneously develop two medically desirable wavelengths (such as 0.532 microns and 2.9 microns) for instantaneously producing medically desired results, such as superior incisions and optimum coagulative ability, with a single tool.

DISCLOSURE OF THE INVENTION

It is an object of this invention to obviate the above-described problems and shortcomings of the laser devices heretofore available in the industry.

It is another object of the present invention to enable a single, solid-state laser device to develop two medically usable light beam wavelengths simultaneously for use in various medical applications.

It is yet another object of the present invention to provide a device which can be used in conjunction with commercially available solid-state laser devices to enable production of a dual wavelength output from a single wavelength input.

It is also an object of the present invention to provide a laser conversion system which can be utilized in conjunction with a laser light source to develop a laser radiation output having two predetermined wavelengths which are provided coaxially and are endoscopically compatible.

It is an object of this invention to provide a method for providing laser radiation at two predetermined wavelengths for simultaneous use in surgical applications to enable substantially blood-less surgery.

It is yet another object of the present invention to provide a solid-state laser conversion system which can produce a coaxial laser light beam having a predetermined and controllable mix of two or more wavelengths from a single laser source for simultaneous use in medical applications.

In accordance with one aspect of the present invention, there is provided a conversion system for use with commercially available laser devices for medical applications where laser light at a predetermined wavelength is converted for simultaneous coaxial application of laser light at a plurality of predetermined, medically useable wavelengths. The conversion system includes focusing structure for focusing laser radiation at a predetermined pump wavelength into a conversion medium. The conversion medium is prepared for efficient conversion of a portion of the radiation at the input pump wavelength to a signal wavelength, wherein, in one preferred application, either the pump or signal wavelength is in a range of between about 2.7 and about 3.25 microns. The system further includes structure for coaxially transmitting laser radiation at both the pump wavelength and the converted signal wavelength from the conversion system for simultaneous use. In other preferred embodiments, the wavelength of the difference frequency produced by the conversion medium is also in a medically desirable range which can add to the effectiveness of the coaxial pump and signal wavelengths in particular medical applications. The conversion system thereby enables relatively unlimited adaption of commercially available laser devices to optimize the effectiveness and application of such devices in a variety of medical procedures.

BRIEF DESCRIPTION OF THE DRAWINGS

While the specification concludes with claims particularly pointing and distinctly claiming the present invention, it is believed the same will be better understood from the following description taken in conjunction with the accompanying drawings in which:

FIG. 3 is a schematic diagram embodying a conversion system made in accordance with the subject invention;

FIG. 4 is a schematic diagram of a laser system embodying a preferred application of the conversion system of the present invention;

DETAILED DESCRIPTION OF THE INVENTION

Figure 1:
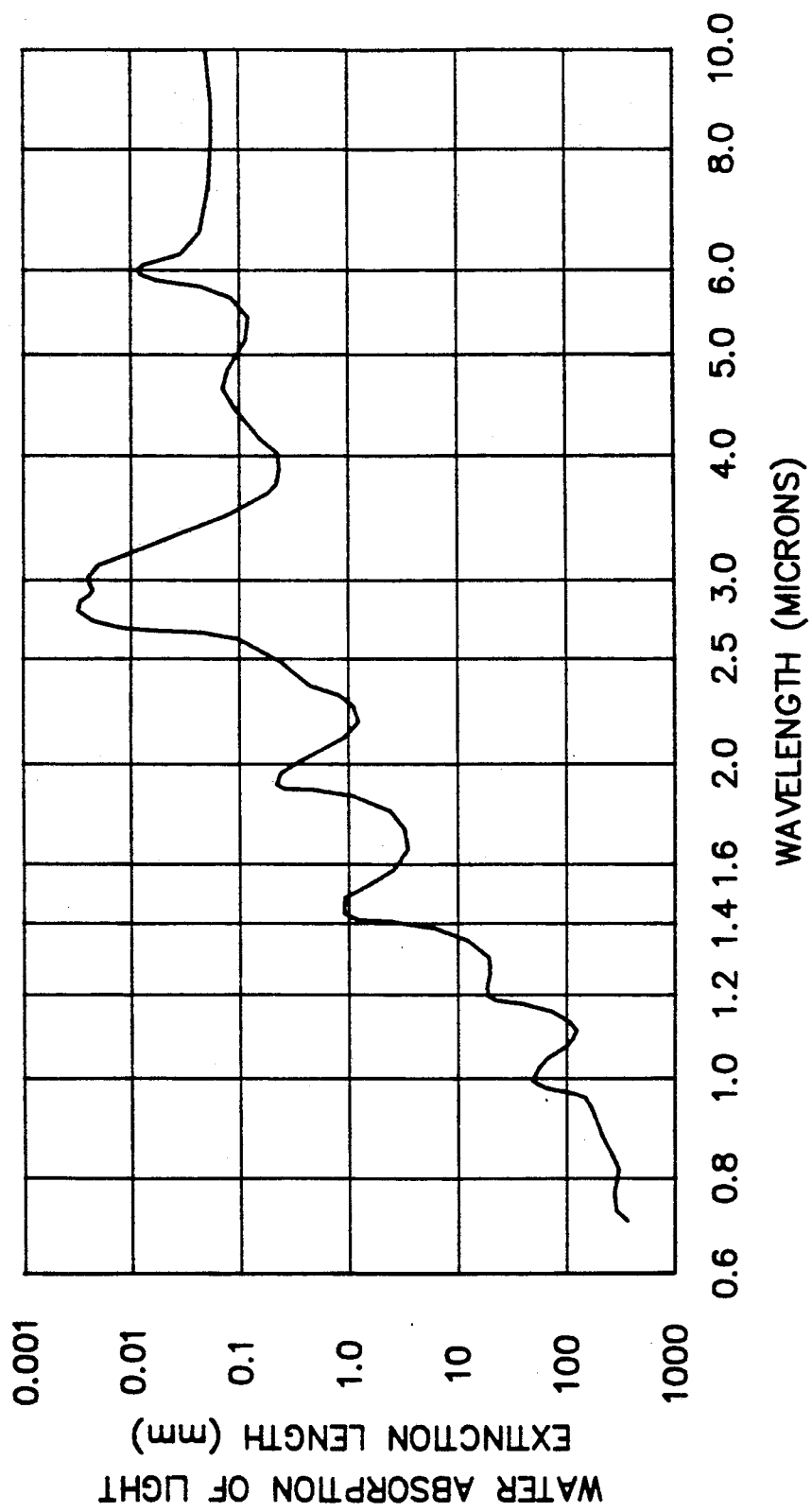
FIG. 1 is a graphical representation of the relationship between water absorption of light radiation (extinction length in mm) at various wavelengths on the spectrum.

Referring now to the drawings in detail, wherein like numerals indicate the same elements throughout the views, and wherein numerals having identical last two elements (e.g. 17, 117, 217) indicate corresponding structures between the various embodiments, FIG. 1 is a graphical representation of the relative absorption levels of light radiation (i.e. the extinction length for diminishing the intensity of entering light down to $e^{-1}$) by water at various wavelengths. As mentioned, because tissue is approximately 80% water, the coefficient of absorption of light energy by water will determine the characteristics of laser interaction in tissue. In order to optimize the efficiency of, for example, cutting or heating of tissue, and to minimize unnecessary tissue damage (such as by thermal damage), an output wavelength closely matched to a water absorption peak should be utilized. FIG. 1 shows that a water absorption peak occurs approximately at a wavelength of between about 2.85 to 2.95 microns, and more generally between about 2.7 and 3.25 microns.

Consequently, the Er:YAG laser is of special interest, since it has an output of approximately 2.9 microns which closely coincides with a water absorption peak. Assuming equal (i.e. time and size) application of laser radiation produced by the Er:YAG at 2.9 microns and radiation produced by a $CO_2$ laser at an output wavelength of 10.6 microns, the thickness of soft tissue damage beneath the excision made by the Er:YAG laser will be much less and preferred over the $CO_2$ laser. However, high quality, reliable pulsing technology is not available for the Er:YAG systems, as the rotating mirror Q-switching technology available is relatively unreliable and inferior to the electro-optic Q-switch technology, such as is available for Nd:YAG systems. The rotating mirror is subject to mirror instability or "wabble", which can cause variance in the beam divergence, spatial profile, and spatial stability. The inconsistency of the resulting radiation energy make this technology unsatisfactory for most micro-surgical procedures.

To respond to these problems, frequency doubling techniques such as optical parametric oscillators or Raman shifting devices have been utilized to convert light beams at longer wavelengths (e.g. 10.6 micron and 1.064 microns) to shorter wavelengths (e.g. 2.9 microns and 0.532 microns) to provide light radiation at a water absorption peak or in the visible light spectrum. Frequency doubling, however, drastically reduces the power output as a result of the relatively low (e.g. about 70% or less) efficiency of such techniques, in addition to the lack of technology for providing pulsed application of radiation from $CO_2$, Er:YAG and Ho:YAG lasers in order to limit unnecessary thermal damage of the tissue.

Figure 2:
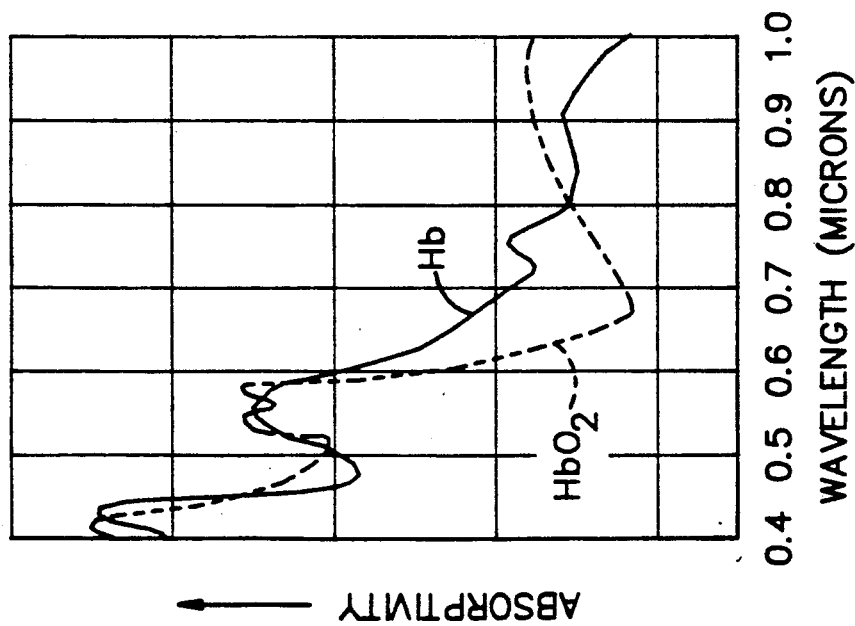
FIG. 2 is a graphical representation of the relative absorption of light radiation by oxygenated and deoxygenated Hemoglobin at various wavelengths on the spectrum.

FIG. 2 illustrates a graph similar to that of FIG. 1, plotting the relative absorption of light by oxygenated ($HbO_2$) and deoxygenated (Hb) Hemoglobin (i.e. blood) for various wavelengths. Since the pertinent absorption peaks for both oxygenated and deoxygenated Hemoglobin are substantially the same, for the purposes of this discussion, both will be jointly considered generally as Hemoglobin. As can be observed, an absorption peak for Hemoglobin occurs within an approximate range of wavelengths between about 0.5 and 0.6 microns. While higher peaks of absorption are present at shorter wavelengths, the peaks at wavelengths less than 0.5 microns are not preferred due to interfering effects of inordinant absorption of shorter wavelength radiation by other aspects of the tissue (e.g. Melanin exhibits enormous absorption of radiation at about 0.4 microns). Radiation in a range of between about 0.5 and 0.6 microns is preferred as it is more transparent to extraneous absorbers such as Melanin. As a consequence, laser radiation in this approximate range provides the most efficient hemostasis control by heating the adjacent blood vessels and augmenting coagulative abilities of the laser tool.

Frequency doubling of the output of an Nd:YAG laser (1.064 microns) can produce radiation at a wavelength of approximately 0.532 microns, which provides very good coagulative abilities. Similarly, a non-solid state dye type laser can produce a light beam having a wavelength of approximately 0.577 microns. An advantage of working with laser light in the visible spectrum (e.g. 0.532 microns or 0.577 microns) is that the beam itself can be seen and there is no need for the use of an additional beam such as a HeNe (Helium Neon) beam to provide visible indication of the light path to assist the surgeon.

Consequently, while devices are available in the industry to provide laser light at the respective absorption peaks for water and for hemoglobin, heretofore each device was particularly designed to provide concentrated laser light output at only a single wavelength. A tradeoff was often required between provision of light radiation at a wavelength which, for example, could provide optimal cutting abilities, and a wavelength which would provide improved coagulative abilities and hemostasis. In fact foresighted experts in this field specifically envisioned the future incorporation of several lasers for simultaneous use. A compound laser system capable of producing a clean incision along with photocoagulative ability and hemostatic control was contemplated as physically incorporating one laser source for cutting (e.g. a $CO_2$ laser or an HF laser), and another shorter wavelength laser source (e.g. the Nd:YAG or argon-ion laser) for hemostatic control However, the slow development of fiber optic delivery systems for the $CO_2$ wavelength lasers, and the impracticality and inadvisability of utilizing the HF laser in an operating room environment have no doubt been factors in preventing such a compound laser from becoming a reality.

The present invention provides a single, solid-state laser conversion system and method for outputting a plurality of predetermined wavelengths (e.g. one wavelength for optional cutting and another for optimal hemostasis) simultaneously and coaxially for convenient use by the surgeon. The multi-wavelength output is a single light beam which can be conveniently focused and directed onto a single target or treatment area for simultaneous application. FIG. 3 illustrates a schematic diagram of a conversion system 10 made in accordance with the subject invention. Conversion system 10 is designed for convenient use with an existing laser system commonly available in the industry, and is contemplated as a relatively low-priced accessory which can be added to a laser system already available in a hospital, clinic, or the like. Such arrangement is seen as providing a low cost way of adapting existing equipment and commercially available laser devices in order to optimize the effectiveness thereof for particular procedures, and to enable application of those devices to a relatively unlimited array of additional medical and surgical procedures.

Conversion system 10 is illustrated as including a focusing device 15 for focusing laser radiation at a predetermined pump wavelength 24 into a conversion medium 40 located within conversion cavity 30. Focusing device 15 can conveniently comprise a beam expander 17 and a collimating lens 19 to focus a laser radiation source beam 22 provided by laser 20 to a predetermined diameter D. Diameter D is determined to appropriately correspond with the cross-sectional area of conversion medium 40, such that the beam 24 of coherent light at a predetermined pump wavelength will be focused to occupy the optimum volume of conversion medium 40 without resulting in undesirable diffraction effects. Focusing device 15 can also preferably provide means for varying the size and direction of pump beam 24 to enable conversion system 10 to be adaptable to a variety of conversion media 40, and to facilitate the adaption of system 10 to provide a variety of predetermined wavelengths, as desired.

Conversion cavity 30 further includes a first window or entrance 32 for receiving laser radiation at a predetermined pump wavelength. While pump wavelength 24 may be identical to the wavelength of source beam 22, it is contemplated that the wavelength of source beam 22 might also be altered (e.g. by frequency doubling from 1.064 microns to 0.532 microns) prior to being focused into conversion cavity 30. First window 32 preferably includes an outer surface 34 treated, coated or otherwise structurally adapted to reduce or eliminate reflection of incident laser radiation at the predetermined pump wavelength, and an inner surface 36 similarly adapted for high transmission of laser radiation at the predetermined pump wavelength and for high reflectivity of the conversion or signal wavelength. Light beam 24 enters conversion cavity 30 and medium 40 for conversion to a signal wavelength in a range of between about 2.7 and 3.25 microns.

Conversion medium 40 can be any structure capable of relatively efficient conversion of a portion of radiation at a predetermined pump wavelength to a predetermined signal wavelength. For example, a pump wavelength of 0.532 microns (a wavelength preferred for good hemostatic control) might be provided, and a portion of the radiation would be converted to a wavelength in a range of between about 2.7 and 3.25 microns (a range preferred for optimal cutting), or vice versa. Because the pump wavelength is preferably predetermined to be medically useable (as used herein the term medically useable shall be understood to mean a wavelength beneficial or desirable for a particular procedure such as cutting, diagnosing, heating, coagulating, or otherwise treating), the output beam is to include a predetermined percentage of radiation at the pump wavelength, and total conversion of the pump wavelength is obviously undesirable. It is preferred that medium 40 comprise an optically non-linear crystal such as the commonly available KTP (as available from Airtron Company in the United States, and FIMS and Shandong University in China).

Conversion medium 40 can also be provided as a Raman cell which, through Raman shifting, can partially convert radiation at a predetermined pump wavelength (e.g. 1.064 or 0.532 microns) to the desired signal range (e.g. between about 2.7 and 3.25 microns). Because the Raman cell will include a gaseous conversion medium (e.g. methane), the light radiation photons will pass through a conversion medium having a much lower density than the KTP material used in the optical parametric oscillator alternative, and the length of conversion medium 40 will necessarily be much longer. The practical difficulties with the Raman approach may indeed make it much less desirable for use as conversion medium 40 than OPO crystals such as KTP, beta-barium-borate (BBO), LAP, $KNbO_3$, or urea. It should also be noted that the conversion medium of the present invention may comprise a plurality of structures such as one or more crystals and/or Raman cells in combination to convert portions of a pump wavelength from a single radiation source into a plurality of medically useable wavelengths as desired.

First window 32 is located at the entrance or proximal end of conversion cavity 30, and a second or transmission window 50 is spaced from window 32 along the longitudinal axis A of cavity 30 and located adjacent the proximal end thereof. Windows 32 and 50 may preferably be formed of material such as calcium fluoride ($CaF_2$). While the conversion efficiency of a conversion crystal such as KTP or BBO generally increases with increased crystal length, it is often desirable to minimize the overall length of an OPO cavity such as conversion cavity 30 for practical application and convenience of the user. In order to provide a conversion cavity with reduced length, it will often be desirable to design the conversion system for ensuring multiple passes of light from laser beam 24 through conversion medium 40 within conversion cavity 30.

In order to provide multiple passes of the light beam through conversion medium 40, second window 50 preferably includes an inner surface 52 prepared for limited transmission (e.g. 20% to 35%) of light at the conversion or signal wavelength (e.g. in a range of between 2.7 and 3.25 microns), and which will be at least partially resonant of radiation at the predetermined pump wavelength (e.g. 1.064 microns). It is important that the inner surface 52 of second window 50 and inner surface 36 of first window 32 provide sufficient resonance of radiation at the predetermined pump wavelength to enable relative efficient conversion of a portion of that pump wavelength radiation to the desired signal wavelength.

Additionally, transmission window 50 has an outer surface 54 which is preferably anti-reflective at the signal wavelength to facilitate transmission of radiation within the desired signal wavelength range from conversion system 10 for use. Consequently, on average, first window 32 and second window 50 provide for limited resonance of light at the predetermined pump wavelength within conversion cavity 30 such that it makes several passes (e.g. 5) through conversion medium 40 before being transmitted through second window 50 for use.

While it is generally desirable to keep the length of conversion cavity 30 to a minimum, the length of this cavity and the average number of passes through conversion medium 40 of light at the pump wavelength will be constrained by the Raleigh length which is related to the diameter of the beam and the wavelength itself. In particular, the Raleigh length is that length at which the light beam begins to spread significantly and the intensity of the light begins to appreciably degrade. The Raleigh length can be determined as follows:

$$\text{Raleigh length} = \frac{\pi W_o^2}{\lambda}$$

Where:
$W_o$ = radius of light beam
$\lambda$ = wavelength of pump beam

As it is understood that the energy of the light beam 24 passing through conversion medium 40 must be focused sufficiently to exceed the threshold level of a particular crystal (e.g. KTP, BBO LiIO$_3$, KNbO$_3$, or BNN), it is important that the length of conversion cavity 30 and the average number of passes of the light radiation within conversion cavity 30 are sufficient to ensure that the light beam remains relatively focused and that the threshold level of energy is maintained for optimum efficiency of conversion. It is important to fill the volume of the conversion medium (e.g. a KTP crystal) as uniformly as possible over its entire length while maintaining the relatively high intensity required for efficient OPO conversion. It is also important that the light beam diameter be small enough relative to the effective "diameter" of conversion medium to minimize effects of diffraction. The elements of focusing device 15 must be properly chosen to expand and collimate the pump light beam 24 so that the light can traverse conversion cavity 30 many times before the diffractive spreading becomes large enough to interfere with the OPO conversion.

As an example, where the total length of conversion system 10, including conversion cavity 30 and focusing device 15, is to be approximately 6 inches (approximately 15.3 cm) for conversion of an Nd:YAG laser providing a source beam 22 and pump beam 24 having a wavelength of 1.064 microns, a KTP crystal with a cross-sectional dimension of 3 mm × 3 mm may be used, and a beam spot size ($W_o$) having a radius of 0.5 mm provided with an on-axis intensity within the KTP crystal of approximately 100 MW/cm$^2$, and with a depth of focus of focusing device 15 at 21 cm. The 0.5 mm radius of pump beam 24 is small enough to obtain the high intensity required for efficient OPO conversion, but is large enough to yield long depth of focus (i.e. the distance the beam travels without appreciable diffraction) and to avoid crystal damage. KTP has a damage threshold (D.T.) of approximately 0.4 GW/cm$^2$ for a 10 ns pulse at 1.064 microns. Consequently, the 100 MW/cm$^2$ intensity is well below the damage threshold for this crystal. BBO has an even higher damage threshold of 5 GW/cm$^2$.

First window 32 and second window 50 are provided to increase the overall conversion efficiency of cavity 30 by reducing the reflection loss experience by the pump light beam at the cavity input, by increasing the average interaction length of the pump light beam with the conversion medium 40, and by increasing the percentage of the conversion or signal wavelength light exiting the cavity's output or distal end. It is also contemplated that the individual elements of focusing device 15 will be provided with anti-reflective surfaces as well to minimize reflection loss.

Light exiting the distal end of conversion cavity 30 (i.e. the output of conversion system 10) comprises a coaxial (e.g. along axis A), multi-wavelength output beam O including the predetermined pump and signal wavelengths. For example, where a pump wavelength of 1.064 microns from an Nd:YAG laser is utilized, a portion of the pump beam wavelength will be downshifted to approximately 2.9 microns by conversion medium 40 (e.g. KTP crystal), and the output O will comprise a light beam having wavelengths of 1.064 and 2.9 microns. Such dual wavelength output can provide clean cuts as a result of its 2.9 micron wavelength, with simultaneous focused and instantaneous coagulative abilities as a result of the shorter 1.064 micron wavelength. The coaxial, single beam compound wavelength output of the present invention obviates a need for aligning separate laser beams from multiple sources, as the output is precisely focused at the target or spot of treatment by the operator.

As indicated above, source beam 22 from an Nd:YAG laser at 1.064 micron wavelength could be frequency doubled prior to its introduction to conversion system 10 such that pump wavelength 24 would be 0.532 microns, and the resulting multi-wavelength output O would comprise light at both the pump wavelength of 0.532 microns and the signal wavelength of 2.9 microns. While frequency doubling of the source beam 22 would tend to reduce the power of pump wavelength 24 and the resulting 0.532 micron portion of output O, it is believed that the power levels obtainable for both wavelengths will be sufficient to provide clean cuts and instantaneous and focused hemostasis control with the use of a single Nd:YAG laser source.

As is also known, however, OPO conversion uses a non-linear crystal to convert light at a pump wavelength into two longer output wavelengths, the signal and the difference frequency or idler frequency. For example, if the signal wavelength is chosen (i.e. by selection of the conversion medium) to lie in the 2.7–3.25 micron range, and the pump wavelength lies between about 0.532 and 1.318 microns, the resulting idler wavelength will always take on a value greater than the pump wavelength but less than that of the signal. Particularly, the idler frequency wavelength is equal to the difference between the signal and pump wavelengths. Therefore, the hemostasis produced by the idler wavelength will be less than that produced by the pump wavelength, and the cutting ability of the idler frequency will be less than that of the signal. In most cases, the idler component of the output does little to enhance the medical efficacy of the system and can be ignored.

There can be applications, however, where the idler or difference frequency may fall within a wavelength range which can indeed add to the effectiveness of the coaxial pump or signal wavelength of the output O of the present invention. One such exception occurs when the pump wavelength is chosen to be 0.532 microns and the idler frequency is approximately 0.583 microns, resulting in a signal output wavelength of about 6.1 microns. Although the 6.1 micron wavelength is not absorbed as strongly by water as the preferred 2.7-3.25 micron wavelength, it is more strongly absorbed than the above-described 10.6 micron $CO_2$ laser output. Additionally the idler wavelength is near the Hemoglobin absorption peaks, thus increasing the hemostasis potential of the system. Consequently, both the idler and pump frequencies would provide medically useable radiation for enhancing hemostatic control, while the signal wavelength is medically useable to simultaneously provide efficient cutting abilities.

Although the relative merits of various candidate wavelength sets must be determined by in vivo testing, this particular combination of wavelengths may represent a preferred choice for many applications. Unfortunately, although the non-linear crystal is available for producing this particular output wavelength set (e.g. $LiNO_3$, $KNbO_3$ or BNN), optical fibers capable of transmitting the 6.1 micron wavelength with low energy loss are only currently being developed. Consequently, optimal implementation of the full variety of applications for the present invention may be delayed until corresponding related technology (e.g. fiberoptics) is available.

It has been found that the optimum conversion utilizing OPO technology occurs when there is an approximate 2:1 ratio between the desired signal or conversion wavelength (e.g. 2.7-3.25 microns) and the pump wavelength (e.g. 1.064). For this reason, because conversion of the 1.064 micron wavelength to an approximate 2.9 micron wavelength is further from the desired ratio (i.e. 1:2) than would be conversion from a modified 1.318 micron Nd:YAG laser pump wavelength to approximately 2.9 microns, it may well be preferred to modify the Nd:YAG laser to provide the 1.318 micron wavelength (i.e. by changing the YAG lasers reflecting mirrors as appropriate). On the other hand, while conversion of the frequency doubled Nd:YAG source beam of 0.532 microns to approximately 2.94 microns (signal wavelength) may result in some energy being wasted due to the inefficiencies of conversion (i.e. not a 1:2 conversion), an optimal pair of cut/seal radiation wavelengths may be obtained in this way. It should be noted that upshift conversion (such as by frequency doubling) of a pump wavelength in a range of between about 2.7 and about 3.25 microns to a signal wavelength in a range of between about 0.5 and about 1.2 microns could equally be effected by the present invention to provide two similarly useful wavelengths simultaneously.

FIG. 4 illustrates a conversion system 110 utilized with a laser 120 in a preferred arrangement. In particular, conversion system 110 is shown as being substantially enclosed within a housing 160 having a receiving means or input opening 161 at its proximal end, and a transmission means or output opening 163 at its distal end. Within housing 160 is located focusing device 115 which can similarly include a beam expander 117 and a collimating lens 119. Conversion cavity 130 is shown as including first window 132, conversion medium 140 (preferably comprising an OPO crystal 141), and a second window 150 similar to the corresponding structure described above with regard to conversion cavity 30. Length L of conversion cavity 130 will similarly be determined in accordance with the discussion above and the Raleigh length limitations. An adjustment device 145, such as a microlinear/rotary stage, is optionally provided to enable tuning of the conversion medium by adjusting its orientation and/or axial position, such as via adjustment knob 146. Phase matching of the non-linear crystal in OPO applications, such as shown and described in U.S. Pat. Nos. 4,639,923 (Tang et al.) and 4,180,751 (Ammann), can be accomplished by adjusting the crystal orientation to "tune" the output wavelengths within a certain range, as desired.

Preferably included within conversion system 110 is a Q-switching device 165 for providing optimal control of the temporal pulse width and size of the dual wavelength output of conversion system 110. Various acoustic-optical and electro-optical Q-switching technology is available in the industry, such as described in U.S. Pat. No. 4,455,657, and will not be discussed in detail herein. Generally, the Q-switch device 165 is utilized as a means for deflecting light photons within conversion cavity 130 to diffuse power from the central axis on an intermittent basis such that concentrated short bursts of dual wavelength laser energy can be provided by conversion system 110 for use in various medical applications. As mentioned, reduction of the temporal length of successive bursts of light energy can correspondingly reduce the size of the zone of thermal damage in laser surgery.

Multi-wavelength light energy O' is produced along axis A' in a manner corresponding with that described above with regard to FIG. 3, and is passed through an optional selective wavelength controller 175, which can comprise a variable filter or, in some cases, a beam splitter. In particular, it is contemplated that in many applications it may be preferred to obtain a predetermined mixture of the several desired wavelengths for very specialized applications. For example, hemostatic control in highly perfused tissue may require a higher concentration of output light in the shorter wavelength zone (i.e., the high blood absorption wavelength), wherein it is preferred to throttle back the percentage of transmitted light at the higher wavelengths (i.e., the output light in the 2.7 to 3.2 micron range). Consequently, while the present invention provides the unique ability to produce a multi-wavelength, coaxial light beam comprising a predetermined mixture of two or more simultaneously applicable wavelengths (e.g. for cutting and instantaneously sealing blood vessels and the like), it further provides an advantageous adaptability of custom mixing the output wavelengths.

As an example, some surgical procedures involve tissue which is relatively bloodless, wherein the shorter wavelength light for coagulative action is not needed. In such a situation, selective wavelength controller 175 could reduce or eliminate the low-water absorption wavelength. In such instances, the output beam O' could be adjusted to a modified output beam M.

Whether or not the output of conversion system 110 is modified by a selective wavelength controller 175, the output of system 110 will preferably be appropriately focused for delivery to a laser tool or the like, such as by beam expander 177, collimator lens 179 and focusing lens 180, as illustrated in FIG. 4.

Figure 5:
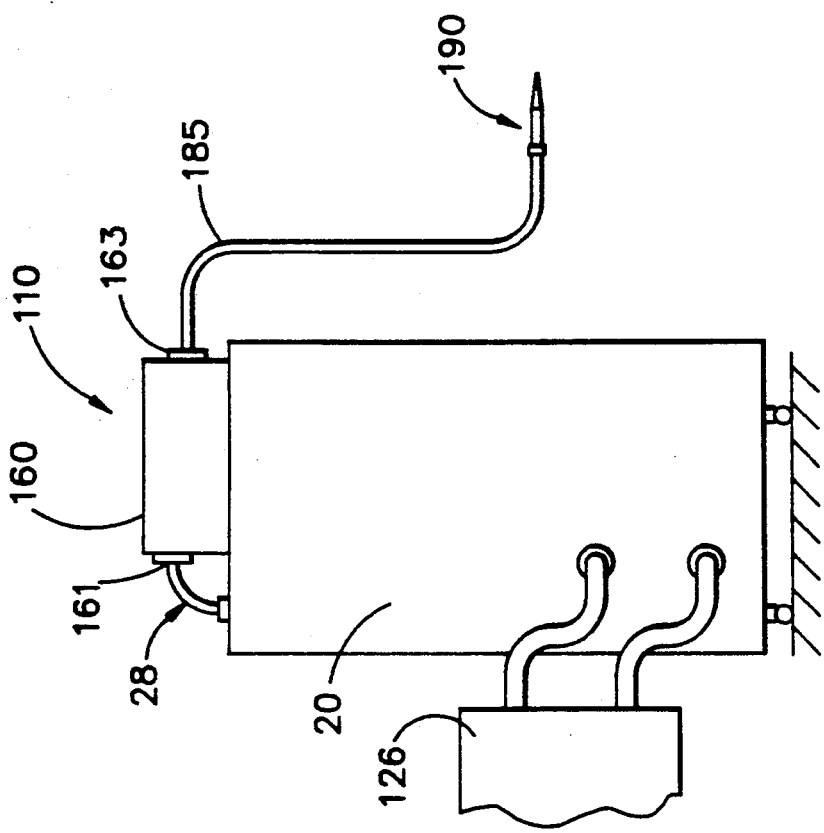
FIG. 5 is a schematic illustration of a typical application of the subject conversion system in connection with a medical laser system.

FIG. 5 illustrates a typical application of the subject conversion system in connection with a laser system 20, such as an Nd:YAG laser arrangement often found in hospitals, clinics and the like. Laser system 20 is shown as including a cooling apparatus 126 such as a water cooling setup, and a source beam delivery apparatus 28, such as a fiber-optic cable. As illustrated, solid-state conversion system 110 would preferably be located adjacent to laser system 20 to receive the source beam via delivery apparatus 28 at input opening 161. Within housing 160 would be located all of the necessary conversion elements as described above with respect to FIG. 4, and the multi-wavelength, coaxial output beam O' (or the modified output beam M) would be transmitted from conversion system 110 through output opening 163.

A set of lenses such as described above with regard to beam expander 177, lens 179 and focusing lens 180 would preferably provide for efficient coupling of the multi-wavelength output beam into an optical fiber cable 185 for convenient transmission to a remote laser tool 190. As described above, conversion system 110 can be specifically set up and adapted to work in conjunction with a variety of solid-state and dye laser devices currently available in the industry such as the Nd:YAG laser. By a combination of manipulation of the source beam (e.g. frequency doubling) and appropriate adaption of the conversion cavity of conversion system 110, a predetermined pair of wavelengths comprising one wavelength in a range of between about 2.7 and 2.9 microns (i.e., a wavelength near the absorption peak of water) and a second shorter wavelength near the absorption peak of Hemoglobin is produced in a preferred embodiment.

Figure 6:
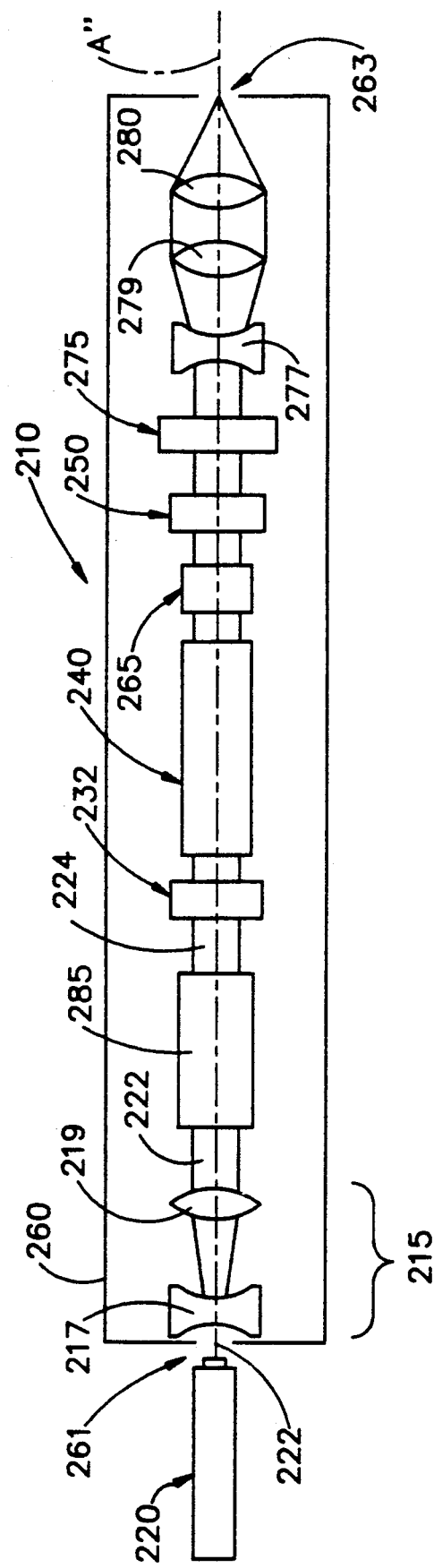
FIG. 6 is a schematic illustration of an alternate embodiment of the subject conversion system.

FIG. 6 schematically illustrates yet another alternate embodiment of a conversion system 210 made in accordance with the subject invention, including elements corresponding to each of the elements described above with regard to FIG. 4, with the addition of an optical frequency doubler or frequency doubling device 285 to modify the source beam 222 to a predetermined pump wavelength beam 224. It is contemplated that it will be preferred to focus source beam 222 (such as via focusing device 215) prior to its introduction into frequency doubling device 285, as illustrated. An arrangement as shown in FIG. 6 could be utilized to convert the source beam 222 from an Nd:YAG laser 220 at a wavelength of 1.064 microns into a pump beam 224 having a wavelength of 0.532 microns, as mentioned above.

The balance of conversion system 210 would preferably include corresponding structure and operate as described above with regard to the embodiment 110 of FIG. 4. As in the other embodiments, the multi-wavelength output light beam, having a combination of wavelengths such as 0.532/2.9 microns, 1.32/2.9 microns, 1.064/2.9 microns, 0.532/6.1 (with 0.583 idler) microns, or 0.532/2.3 (with 0.630-0.690 idler) microns, will be provided through output opening 263, which can be directly coupled to an optical fiber (e.g. 185) for delivering the multi-wavelength output to the target for simultaneous use.

It is further contemplated that the receiving means or input opening (e.g. 61, 161, 162) of the subject conversion system can also be fitted with fiber-optic or mechanical attachment means for facilitating relatively quick attachment of the conversion system to existing Nd:YAG or KTP medical laser systems commonly used in the industry. As such, the multi-functional conversion system can provide a valuable aftermarket or add-on device capable of enhancing and expanding the useful application of any particular laser system.

The solid-state conversion system of the present invention will preferably be assembled and designed for use with a particular laser device to provide a coaxial light beam output having a predetermined plurality of medically useable wavelengths chosen to provide, for example, both superior cutting and coagulative abilities simultaneously. In this way, precise assembly and adjustment of the conversion medium (such as an OPO crystal) can be accomplished in the factory. Because the angle of cut and the angle of orientation of any particular OPO crystal is quite important in providing an OPO resonant cavity and conversion assembly, precise orientation of the crystal can be accomplished during assembly by utilization of an adjustable mount or mounting device (e.g. a microlinear/rotary stage device 145) so that the conversion system can be tested and appropriately adjusted prior to completion of the assembly process. As indicated, means for adjusting the crystal position and orientation can equally be provided as part of the conversion system itself to allow for field tuning as well.

The subject conversion system results in the unique provision of a single output beam which can, in a preferred example, include a predetermined mixture of light energy at a first wavelength that is much more strongly absorbed by water, and at a second wavelength which is much more strongly absorbed by blood, at a common tip for simultaneous use. This unique combination of radiation wavelengths can provide optimized tissue cutting abilities with instantaneous coagulative capabilities, resulting in cleaner, faster, safer and essentially "blood-less" surgical procedures.

Some power will inevitably be absorbed and converted into heat within the conversion system, however, such heat within the various components is small enough such that the conversion system can generally be operated without a need for additional means for cooling. It is contemplated that a relatively thin but protective housing (e.g. 60, 160, 260) may be utilized which itself can facilitate cooling of the system by natural convection/heat exchange processes. While additional cooling structure is not believed necessary, the addition of such could be simply accomplished if desired by a variety of means available to those or ordinary skill.

The present invention can similarly be used for other medical treatment and/or diagnostic purposes. For example, photodynamic therapy (PDT) utilizes relatively low intensities of laser light, in combination with a photosensitizing agent such as hematoporphryin derivative ($H_pD$) to disrupt the vasculature of tumors. Typically, PDT involves application of light in the range of between about 0.630 and about 0.690 microns which is absorbed by the photosensitive material to effectively destroy the tumor. It has been determined that in many cases PDT is enhanced by hyperthermia. Some researchers have utilized two separate lasers, one emitting light at 0.630 microns and the other a Nd:YAG laser operating at 1.064 microns, in order to combine the PDT and hyperthermia treatments. The present invention can accomplish both simultaneously with a single laser by (for example) first frequency-doubling a 1.064 micron laser beam to 0.532 microns, then providing a conversion medium to provide an idler frequency in a range of between about 0.630 and about 0.690 microns (depending upon the particular photosensitizing agent used), as well as light at a signal wavelength in the 2.3 to 3.4 micron range. The infrared light is suitable to induce hyperthermia as it is more strongly absorbed by the water content.

In this fashion, a single laser can be used for the combined instantaneous treatment, eliminating the difficulties of alignment of two separate beams and the extra cost associated with two lasers. The combined treatment is precise because the various wavelengths are simultaneously applied to the exact treatment area or target. Additionally, the laser devices currently used to provide light at 0.630–0.690 microns is an Argon-dye laser, which is very large and unwieldy to work with because of the laborious dye changing requirements. The present conversion system obviates these problems, and enables use of commonly available 1.064 Nd:YAG devices. It is believed that there are numerous other procedures which require a plurality of treatments which could be simultaneously provided from a single laser source via the subject conversion system and method in similar fashion.

As mentioned, a selective wavelength controller (e.g. 175) can be utilized to remove some percentage of the pump wavelength from the output beam, such as to provide a relatively higher concentration of one or more of the outer wavelengths as desired. For example, depending upon the type of target tissue (e.g. corneal, cartilage, skin, muscle, organ, etc.), the surgeon may choose to reduce some portion of the wavelength(s) which will be generally more strongly absorbed by blood. Tissue prone to greater blood loss will require a higher percentage of the wavelength in the shorter range (e.g. 0.5–1.2 microns) than tissue such as cartilage or corneal tissue. In surgical procedures on corneal tissue, it may be preferred to completely eliminate the shorter wavelength, as such surgery is essentially bloodless. A single conversion system made in accordance with the subject invention can be fitted with replaceable or variable filtering lenses to allow a wide variety of mixtures of the resulting wavelengths for all of these applications.

Having shown and described the preferred embodiments of the present invention, further adaptions of the conversion system and method described herein can be accomplished by appropriate modifications by one of ordinary skill in the art without departing from the scope of the present invention. Several of these potential modifications have been mentioned, and others will be apparent to those skilled in the art. For example, in particular arrangements, it may be preferred to attach first window 32 and second window 50 immediately adjacent to the proximal and distal ends of conversion medium 40. This could also be accomplished by direct application of an appropriate coating surface to each of the proximal and distal ends of conversion medium 40 to eliminate a need for independent optical devices, to minimize the overall length of conversion cavity 30, or to eliminate unnecessary interfaces between optical components and various air spaces. As indicated, the variety of applications for converting a single wavelength laser beam into a single controllable beam including two or more medically useable wavelengths for simultaneous, coaxial use is virtually unlimited. Several varied applications have been mentioned herein, and others will become apparent to those of ordinary skill in the art. Accordingly, the scope of the present invention should be considered in terms of the following claims and is understood not to be limited to the details of structure and operation shown and described in the specification and drawings.

I claim:

1. A conversion system for medical applications wherein laser radiation at a predetermined wavelength from a single laser device is converted for simultaneous application of laser light energy at a plurality of predetermined wavelengths, said conversion system comprising:

means for receiving laser radiation at a single predetermined source wavelength from a laser device;

means for focusing received laser radiation at a predetermined pump wavelength into a conversion medium, said pump wavelength being in a range of wavelengths closely matched to a light absorption peak of one of either water or Hemoglobin, for medical use;

a conversion medium prepared for efficient conversion of a portion of said focused radiation at said pump wavelength to a predetermined medically usable signal wavelength, said signal wavelength being in a range of wavelengths closely matched to the other of said water or Hemoglobin light absorption peaks; and means for coaxially transmitting laser radiation at both said pump and signal wavelengths from said conversion system for simultaneous use in a medical procedure.

2. The conversion system of claim 1, wherein said range of wavelengths closely matched to a light absorption peak of water is between about 2.7 and 3.25 microns, and said range of wavelengths closely matched to a light absorption peak of Hemoglobin is between about 0.5 and about 1.2 microns.

3. The conversion system of claim 1, wherein said conversion medium comprises a non-linear crystal, and wherein said pump wavelength is in a range of between about 2.7 and about 3.25 microns.

4. The conversion system of claim 1, wherein said conversion medium comprises a Raman cell device, and wherein said pump wavelength is in a range of wavelengths closely matched to a light absorption peak of Hemoglobin of between about 0.5 and about 1.2 microns, and said signal wavelength is in a range of wavelengths closely matched to a light absorption peak of water between about 2.7 and about 3.25 microns.

5. The conversion system of claim 1, wherein said source wavelength is said pump wavelength.

6. The conversion system of claim 1, further comprising means for converting the source wavelength of said laser radiation to said predetermined pump wavelength.

7. The conversion system of claim 6, wherein said means for converting said source wavelength of the laser radiation received from said laser device comprises a frequency doubling device.

8. The conversion system of claim 1, wherein the wavelength of said radiation received from said laser device is one of the following group of approximate wavelengths provided by available commercial laser sources: 0.532 microns, 1.064 microns, 1.32 microns or 1.414 microns.

9. The conversion system of claim 1, wherein said conversion medium is prepared for conversion of a portion of said radiation at said pump wavelength to a plurality of additional medically useable wavelengths, and wherein said transmitting means coaxially transmits said pump and said additional medically useable wavelengths for simultaneous use.

10. The conversion system of claim 1, wherein said pump wavelength is in a range of between about 0.5 and 0.6 microns.

11. A conversion system for medical applications wherein laser radiation at a predetermined wavelength from a single laser device is converted for simultaneous application of laser light energy at a plurality of predetermined wavelengths, said conversion system comprising:
- means for receiving laser radiation at a single predetermined source wavelength from a laser device;
- means for focusing received laser radiation at a predetermined medically usable pump wavelength into a conversion medium;
- a conversion medium prepared for efficient conversion of a portion of said focused radiation at said pump wavelength to a predetermined medially usable signal wavelength;
- means for coaxially transmitting laser radiation at both said pump and signal wavelengths from said conversion system; and
- wherein said pump wavelength is approximately 0.532 microns, and said conversion medium is prepared to convert a portion of said pump wavelength radiation into a signal wavelength of approximately 6.1 microns and a difference frequency of approximately 0.583 microns, and wherein radiation at the pump, signal and difference frequency wavelengths is coaxially transmitted for simultaneous use.

12. A conversion system for medical applications wherein laser radiation at a predetermined wavelength from a single laser device is converted for simultaneous application of laser light energy at a plurality of predetermined wavelengths, said conversion system comprising:
- means for receiving laser radiation at a single predetermined source wavelength from a laser device;
- means for focusing received laser radiation at a predetermined medically usable pump wavelength into a conversion medium;
- a conversion medium prepared for efficient conversion of a portion of said focused radiation at said pump wavelength to a predetermined medially usable signal wavelength;
- means for coaxially transmitting laser radiation at both said pump and signal wavelengths from said conversion system; and
- wherein said pump wavelength is approximately 0.532 microns, and said conversion medium is prepared for conversion of a portion of said radiation at pump wavelength to a signal wavelength in a range of between about 2.3 and about 3.4 microns and a difference frequency in a range of between about 0.630 and about 0.690 microns, and wherein radiation at the pump, signal and difference frequency wavelength is coaxially transmitted for simultaneous use.

13. A solid-state conversion system for medical application wherein laser radiation at a predetermined wavelength from a single laser device is converted for simultaneous application of laser light energy at a plurality of predetermined wavelengths, said conversion system comprising:
- means for receiving laser radiation at a single predetermined source wavelength from a laser device;
- means for focusing received laser radiation at a predetermined pump wavelength into a conversion medium, said pump wavelength being in a range of wavelengths closely matched to a light absorption peak of water between about 2.7 and about 3.25 microns;
- a conversion medium prepared for efficient conversion of a portion of said focused radiation at said pump wavelength to a predetermined medically usable signal wavelength, said signal wavelength being in a range of wavelengths closely matched to a light absorption peak of Hemoglobin between about 0.5 and about 1.2 microns; and
- means for coaxially transmitting laser radiation at both said pump and signal wavelengths from said conversion system for simultaneous use in a medical procedure.

14. The conversion system of claim 13, further comprising means for controlling the relative percentages of coherent light at the pump and signal wavelengths which are coaxially transmitted from said system for simultaneous use.

15. The conversion system of claim 14, wherein said means for controlling the relative percentages of coherent light comprises a filtering device.

16. The conversion system of claim 13, further comprising means for attaching the conversion system to a single source of coherent light.

17. The conversion system of claim 13, further comprising pulsing means for selectively temporally limiting the transmission of said coaxial pump and signal wavelength coherent light from said system to predetermined intermittent pulses.

18. A method for converting radiation at a single predetermined wavelength to coaxial coherent light at a plurality of predetermined wavelengths for simultaneous use in medical applications, said method comprising the steps of:
- receiving coherent light at a predetermined source wavelength from a light source;
- focusing said coherent light at a predetermined medically usable pump wavelength into a conversion cavity, said pump wavelength being in a range of wavelengths closely matched to a light absorption peak of one of either water or Hemoglobin;
- converting a portion of said coherent light at said pump wavelength to coherent light at a predetermined medically usable signal wavelength, said signal wavelength being in a range of wavelengths closely matched to the other of said water or Hemoglobin light absorption peaks;
- coaxially transmitting coherent light at both said pump and signal wavelengths from said system for simultaneous use.

19. The method of claim 18, further comprising the step of converting coherent light received at said predetermined source wavelength to coherent light at a predetermined pump wavelength.

20. The method of claim 18, further comprising the step of controlling the relative percentages of coherent light at said pump and signal wavelengths which are coaxially transmitted from said system for use.

21. The method of claim 18, wherein said step of converting a portion of said coherent light at said pump wavelength to coherent light at said signal wavelength comprises passing said coherent light through a non-linear crystal within said cavity.

22. The method of claim 21, wherein at least a portion of said coherent light is passed through said non-linear crystal within said cavity a plurality of times.

23. The method of claim 18, further comprising the step of temporally controlling the output of coherent light transmitted from said system such that said light at said plurality of predetermined wavelengths is transmitted in successive short pulses for use.

24. The conversion system of claim 18, wherein said range of wavelengths closely matched to a light absorption peak of water is between about 2.7 and about 3.25 microns, and said range of wavelengths closely matched to a light absorption peak of Hemoglobin is between about 0.5 and about 1.2 microns.

25. A method for converting radiation at a single predetermined wavelength to coaxial coherent light at a plurality of predetermined wavelengths for simultaneous use in medical applications, said method comprising the steps of:
- receiving coherent light at a predetermined source wavelength from a light source;
- focusing said coherent light at a predetermined medically usable pump wavelength into a conversion cavity;
- converting a portion of said coherent light at said pump wavelength to coherent light at a predetermined medically usable signal wavelength and at a predetermined idler frequency; and
- coaxially transmitting coherent light a said pump, signal and idler frequency wavelengths from said system for simultaneous use.

26. The method of claim 25, wherein said signal wavelength is in a range of between about 0.5 and about 1.2 microns, and said pump wavelength is in a range of between about 2.7 and about 3.25 microns.

27. The method of claim 25, wherein said pump wavelength is in a range of between 0.5 and about 1.2 microns, and said signal wavelength is in a range of between about 2.7 and about 3.25 microns.

28. A conversion system for medical applications wherein laser radiation at a predetermined wavelength from a single laser device is converted for simultaneous application of laser light energy at a plurality of predetermined wavelengths, said conversion system comprising:
- means for receiving laser radiation at a single predetermined source wavelength from a laser device;
- means for focusing received laser radiation at a predetermined medically usable pump wavelength into a conversion medium;
- a conversion medium prepared for efficient conversion of a portion of said focused radiation at said pump wavelength to a predetermined medically usable signal wavelength and a difference frequency equal to the difference between the signal and pump wavelengths; and
- means for coaxially transmitting laser radiation at said pump, signal and difference frequency wavelengths from said conversion system, for simultaneous use in a medical procedure.

29. The conversion system of claim 28, further comprising means for controlling the relative percentages of laser radiation of each of said pump, signal and difference frequency wavelengths from said system for use.

30. A solid-state conversion system for medical applications wherein laser radiation at a predetermined wavelength from a single laser device is converted for simultaneous application of laser light energy at a plurality of predetermined wavelengths and wherein said medical applications may involve the use of a particular drug or agent, said conversion system comprising:
- means for receiving laser radiation at a single predetermined source wavelength from a laser device;
- means for focusing received laser radiation at a predetermined medically usable pump wavelength into a conversion medium;
- a conversion medium comprising a non-linear optical parametric oscillator prepared for efficient conversion of a portion of said focused radiation at said pump wavelength to a predetermined medically usable signal wavelength and for providing multi-wavelength laser radiation output, said output comprising a signal wavelength being in the range of wavelengths more strongly absorbed by water, and at least a second wavelength in a range of wavelengths matched either to a light absorption peak of Hemoblobin or to a light absorption peak of said particular drug or agent; and
- means for coaxially transmitting laser radiation at both said signal and second wavelengths from said conversion system for simultaneous use in a medical procedure.

31. The conversion system of claim 30, wherein said medical application comprises photodynamic therapy in combination with a photosensitizing agent, and wherein said conversion medium converts a portion of said pump wavelength into a signal wavelength in a range more strongly absorbed by water to induce hyperthermia, and a second idler frequency in a range of wavelengths matched to an absorption peak of said photosensitizing agent.

32. The conversion system of claim 31, wherein said idler frequency is in a range of wavelengths between about 0.630 and about 0.690 microns.

* * * * *